(12) United States Patent
Levi

(10) Patent No.: US 11,432,923 B2
(45) Date of Patent: Sep. 6, 2022

(54) FLEXIBLE COMMISSURE FRAME

(71) Applicant: Edwards Lifesciences Corporation, Irvine, CA (US)

(72) Inventor: Tamir S. Levi, Zikhron Yaakov (IL)

(73) Assignee: Edwards Lifesciences Corporation, Irvine, CA (US)

( * ) Notice: Subject to any disclaimer, the term of this patent is extended or adjusted under 35 U.S.C. 154(b) by 290 days.

(21) Appl. No.: 16/112,556

(22) Filed: Aug. 24, 2018

(65) Prior Publication Data

US 2018/0360603 A1 Dec. 20, 2018

Related U.S. Application Data

(63) Continuation of application No. 14/625,344, filed on Feb. 18, 2015, now Pat. No. 10,058,420.

(60) Provisional application No. 61/941,123, filed on Feb. 18, 2014.

(51) Int. Cl.
  *A61F 2/24* (2006.01)
(52) U.S. Cl.
  CPC .................. *A61F 2/2418* (2013.01)
(58) Field of Classification Search
  CPC ........ A61F 2/24; A61F 2/2418; A61F 2/2427; A61F 2/2409
  See application file for complete search history.

(56) References Cited

U.S. PATENT DOCUMENTS

| | | | |
|---|---|---|---|
| 3,755,823 A | 9/1973 | Hancock | |
| 4,035,849 A | 7/1977 | Angell et al. | |
| 4,777,951 A | 10/1988 | Cribier et al. | |
| 4,787,899 A | 11/1988 | Lazarus | |
| 4,796,629 A | 1/1989 | Grayzel | |
| 4,856,516 A | 8/1989 | Hillstead | |
| 4,878,495 A | 11/1989 | Grayzel | |
| 4,966,604 A | 10/1990 | Reiss | |
| 4,994,077 A | 2/1991 | Dobben | |

(Continued)

FOREIGN PATENT DOCUMENTS

| CN | 103237524 A | 8/2013 |
|---|---|---|
| DE | 19532846 A1 | 3/1997 |

(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.

(Continued)

*Primary Examiner* — Christopher D. Prone
(74) *Attorney, Agent, or Firm* — Klarquist Sparkman, LLP; Joel B. German

(57) ABSTRACT

Prosthetic devices and frames for implantation at a cardiac valve annulus are provided that include an annular frame (having an inflow end and an outflow end) and a plurality of axial frame members that bridge two circumferentially extending rows of angled struts. The axial frame members can include a plurality of axially extending leaflet attachment members and a plurality of axial struts in a 1:1 ratio. Along each of the two rows, the frame can have at least three angled struts between adjacent axial frame members.

24 Claims, 6 Drawing Sheets

(56) References Cited

U.S. PATENT DOCUMENTS

| | | |
|---|---|---|
| 5,059,177 A | 10/1991 | Towne |
| 5,192,297 A | 3/1993 | Hull |
| 5,282,847 A | 2/1994 | Trescony et al. |
| 5,370,685 A | 12/1994 | Stevens |
| 5,411,552 A | 5/1995 | Andersen et al. |
| 5,545,214 A | 8/1996 | Stevens |
| 5,554,185 A | 9/1996 | Block et al. |
| 5,558,644 A | 9/1996 | Boyd et al. |
| 5,584,803 A | 12/1996 | Stevens et al. |
| 5,591,195 A | 1/1997 | Taheri et al. |
| 5,607,464 A | 3/1997 | Trescony et al. |
| 5,665,115 A | 9/1997 | Cragg |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,925,063 A | 7/1999 | Khosravi |
| 6,027,525 A | 2/2000 | Suh et al. |
| 6,168,614 B1 | 1/2001 | Andersen et al. |
| 6,221,091 B1 | 4/2001 | Khosravi |
| 6,245,102 B1 | 6/2001 | Jayaraman |
| 6,302,906 B1 | 10/2001 | Goecoechea et al. |
| 6,425,916 B1 | 7/2002 | Garrison et al. |
| 6,454,799 B1 | 9/2002 | Schreck |
| 6,458,153 B1 | 10/2002 | Bailey et al. |
| 6,461,382 B1 | 10/2002 | Cao |
| 6,482,228 B1 | 11/2002 | Norred |
| 6,527,979 B2 | 3/2003 | Constantz |
| 6,582,462 B1 | 6/2003 | Andersen et al. |
| 6,652,578 B2 | 11/2003 | Bailey et al. |
| 6,730,118 B2 | 5/2004 | Spenser et al. |
| 6,733,525 B2 | 5/2004 | Yang et al. |
| 6,767,362 B2 | 7/2004 | Schreck |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 7,018,406 B2 | 3/2006 | Seguin et al. |
| 7,018,408 B2 | 3/2006 | Bailey et al. |
| 7,276,078 B2 | 10/2007 | Spenser et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,585,321 B2 | 9/2009 | Cribier |
| 7,618,446 B2 | 11/2009 | Andersen et al. |
| 7,655,034 B2 | 2/2010 | Mitchell et al. |
| 7,785,366 B2 | 8/2010 | Maurer et al. |
| 7,959,672 B2 | 6/2011 | Salahieh et al. |
| 7,972,378 B2 | 7/2011 | Tabor et al. |
| 7,993,394 B2 | 8/2011 | Hariton et al. |
| 8,029,556 B2 | 10/2011 | Rowe |
| 8,133,270 B2 | 3/2012 | Kheradvar et al. |
| 8,167,932 B2 | 5/2012 | Bourang |
| 8,449,606 B2 | 5/2013 | Eliasen et al. |
| 2002/0026094 A1 | 2/2002 | Roth |
| 2002/0032481 A1 | 3/2002 | Gabbay |
| 2002/0138135 A1 | 9/2002 | Duerig et al. |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0075728 A1 | 4/2005 | Nguyen et al. |
| 2005/0096736 A1 | 5/2005 | Osse et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2005/0267560 A1 | 12/2005 | Bates |
| 2006/0025857 A1 | 2/2006 | Bergheim et al. |
| 2006/0058872 A1 | 3/2006 | Salahieh et al. |
| 2006/0095115 A1* | 5/2006 | Bladillah ............ A61F 2/2418 623/1.16 |
| 2006/0122692 A1* | 6/2006 | Gilad ................. A61F 2/2418 623/1.24 |
| 2006/0122693 A1 | 6/2006 | Biadillah et al. |
| 2006/0149350 A1 | 7/2006 | Patel et al. |
| 2006/0178740 A1* | 8/2006 | Stacchino ............ A61F 2/848 623/2.18 |
| 2007/0005131 A1 | 1/2007 | Taylor |
| 2007/0010877 A1 | 1/2007 | Salahieh et al. |
| 2007/0112422 A1 | 5/2007 | Dehdashtian |
| 2007/0203503 A1 | 8/2007 | Salahieh et al. |
| 2007/0203575 A1 | 8/2007 | Forster et al. |
| 2007/0265700 A1 | 11/2007 | Eliasen et al. |
| 2008/0114442 A1 | 5/2008 | Mitchell et al. |
| 2008/0125853 A1 | 5/2008 | Bailey et al. |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0319037 A1 | 12/2009 | Rowe et al. |
| 2010/0049313 A1 | 2/2010 | Alon et al. |
| 2010/0198347 A1 | 8/2010 | Zakay et al. |
| 2011/0015729 A1 | 1/2011 | Jimenez et al. |
| 2012/0123529 A1 | 5/2012 | Levi et al. |
| 2012/0172978 A1 | 7/2012 | DuMontelle |
| 2012/0197391 A1 | 8/2012 | Alkhatib et al. |
| 2013/0023985 A1 | 1/2013 | Khairkhahan et al. |
| 2013/0032511 A1 | 2/2013 | Wilson |
| 2013/0317598 A1 | 11/2013 | Rowe et al. |
| 2013/0325114 A1 | 12/2013 | McLean et al. |

FOREIGN PATENT DOCUMENTS

| | | |
|---|---|---|
| DE | 19546692 A1 | 6/1997 |
| DE | 19857887 A1 | 7/2000 |
| DE | 19907646 A1 | 8/2000 |
| EP | 0103546 A1 | 3/1984 |
| EP | 0592410 A1 | 4/1994 |
| EP | 0597967 A1 | 5/1994 |
| EP | 0850607 A1 | 7/1998 |
| EP | 1796597 A2 | 6/2007 |
| FR | 2788217 A1 | 7/2000 |
| FR | 2815844 A1 | 5/2002 |
| JP | 2013543406 A | 12/2013 |
| SU | 1271508 A1 | 11/1986 |
| WO | 9117720 A1 | 11/1991 |
| WO | 9301768 A1 | 2/1993 |
| WO | 98/29057 A1 | 7/1998 |
| WO | 9940964 A1 | 8/1999 |
| WO | 9947075 A1 | 9/1999 |
| WO | 2000041652 A1 | 7/2000 |
| WO | 0149213 A2 | 7/2001 |
| WO | 0154625 A1 | 8/2001 |
| WO | 0162189 A1 | 8/2001 |
| WO | 0047139 A9 | 9/2001 |
| WO | 0164137 A1 | 9/2001 |
| WO | 0176510 A2 | 10/2001 |
| WO | 0222054 A1 | 3/2002 |
| WO | 0236048 A1 | 5/2002 |
| WO | 0247575 A2 | 6/2002 |
| WO | 03047468 A1 | 6/2003 |
| WO | 2005034812 A1 | 4/2005 |
| WO | 2005084595 A1 | 9/2005 |
| WO | 2005102015 A2 | 11/2005 |
| WO | 2006111391 A1 | 10/2006 |
| WO | 2006138173 A2 | 12/2006 |
| WO | 2007047488 A2 | 4/2007 |
| WO | 2007067942 A1 | 6/2007 |
| WO | 2007097983 A2 | 8/2007 |
| WO | 2007142935 A1 | 12/2007 |
| WO | 2008005405 A2 | 1/2008 |
| WO | 2008091515 A2 | 7/2008 |
| WO | 2009033469 A1 | 3/2009 |
| WO | 2009042196 A3 | 6/2009 |
| WO | 2009149462 A2 | 12/2009 |
| WO | 2010121076 A2 | 10/2010 |
| WO | 2010141847 A1 | 12/2010 |

(56) References Cited

FOREIGN PATENT DOCUMENTS

WO          2012048035 A2    4/2012
WO          2013155474 A1    10/2013

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

International Search Report from corresponding PCT case No. PCT/US2015/016367 dated Apr. 29, 2015.

Supplementary Partial EP Search Report for Application No. EP 15 75 2088 Completed Nov. 1, 2017.

International Office Action for International Application No. 2016-569582; dated Dec. 3, 2018.

* cited by examiner

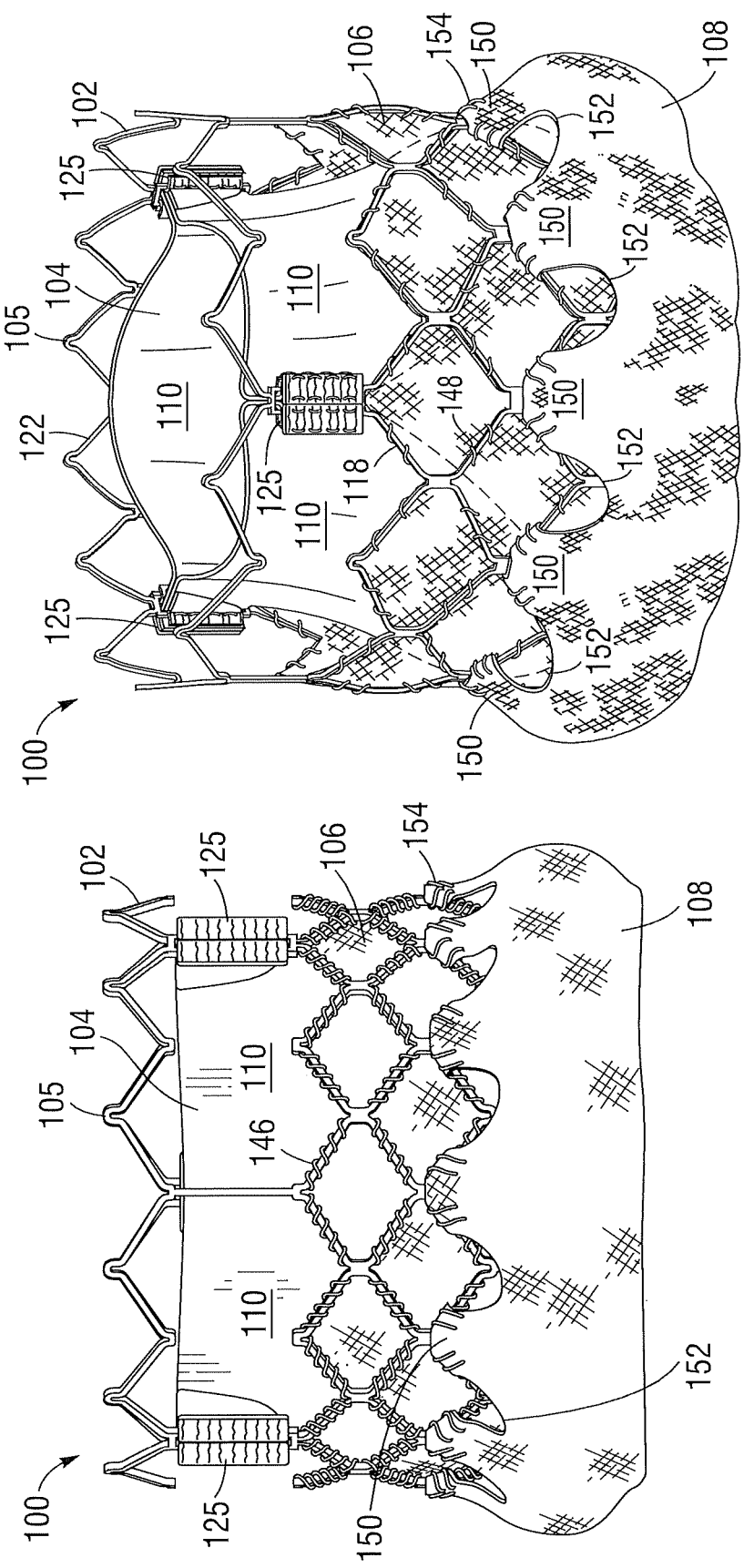

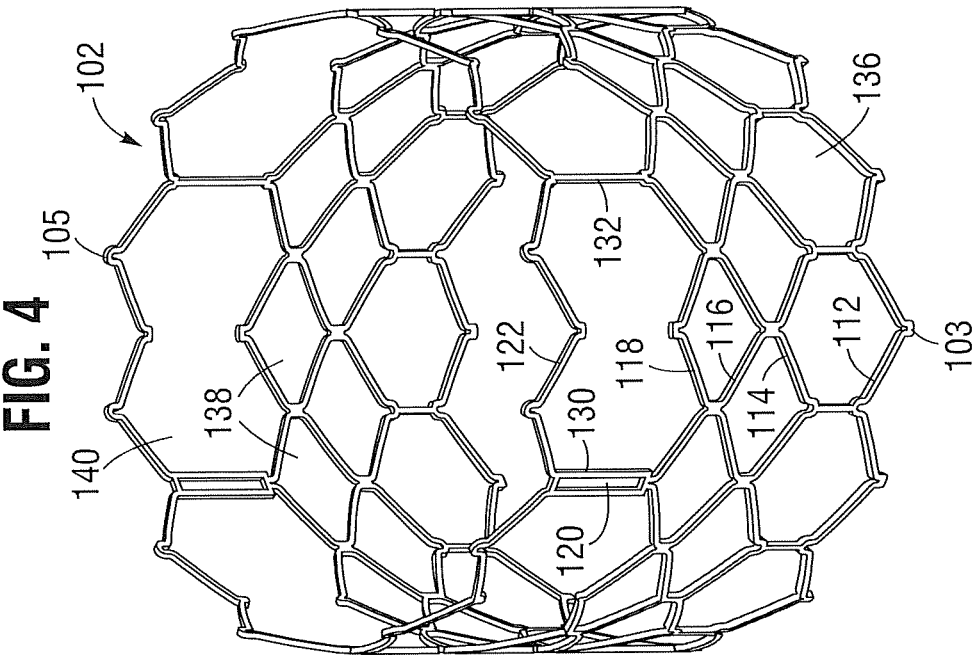
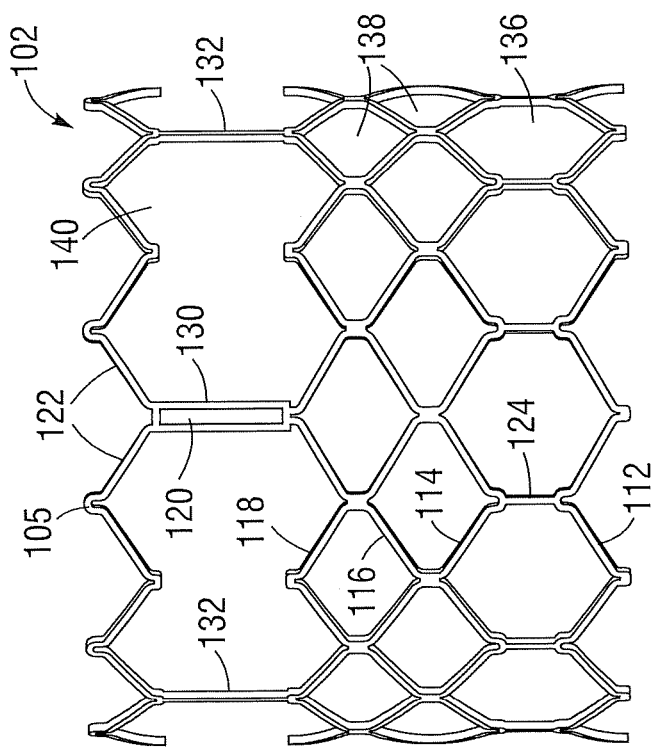

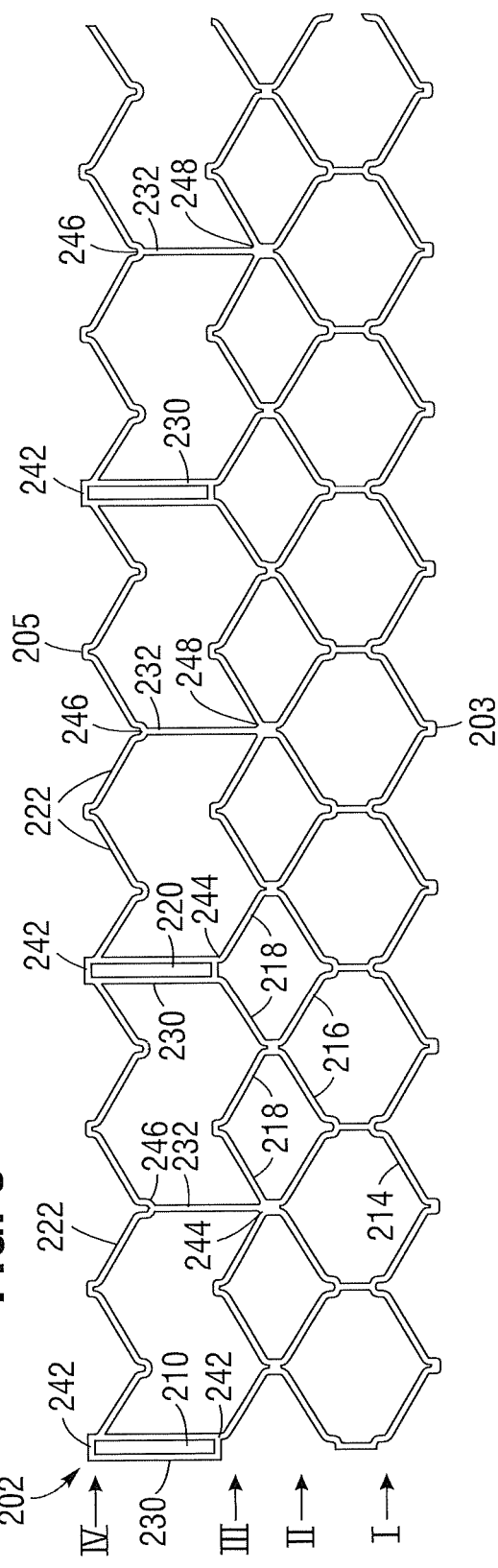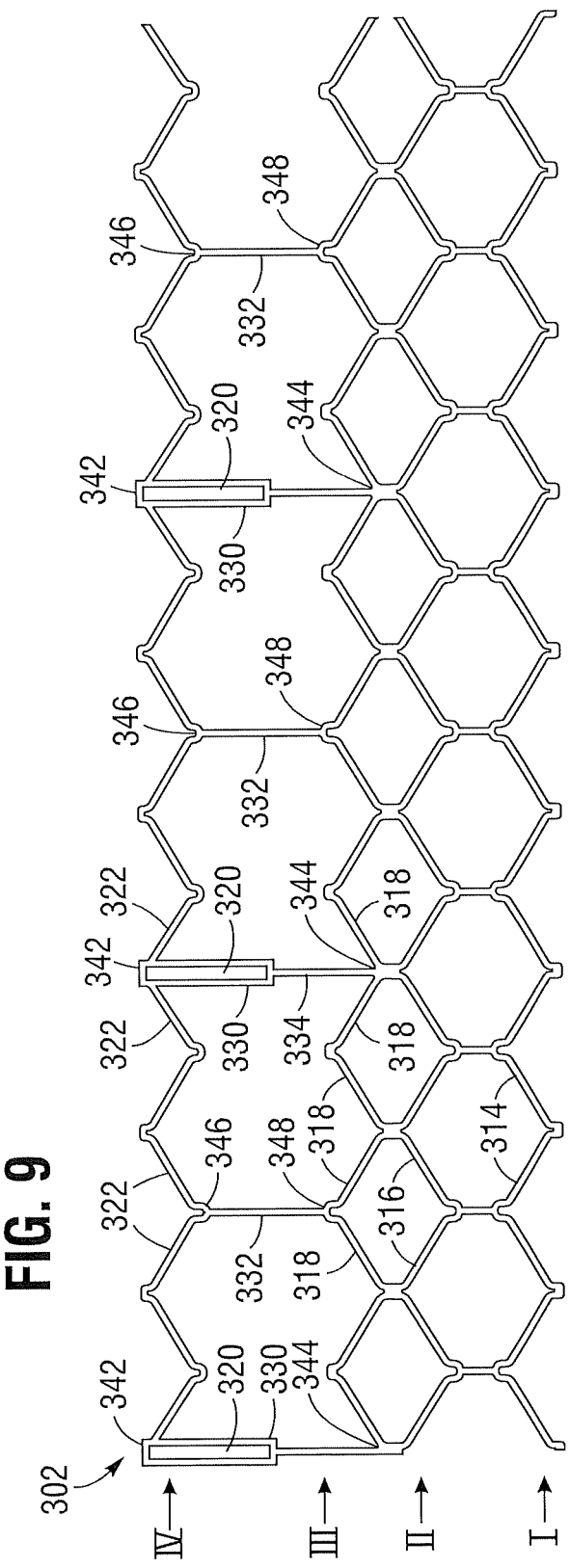

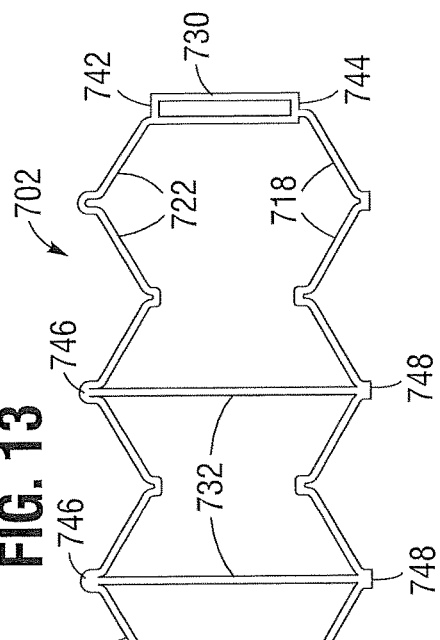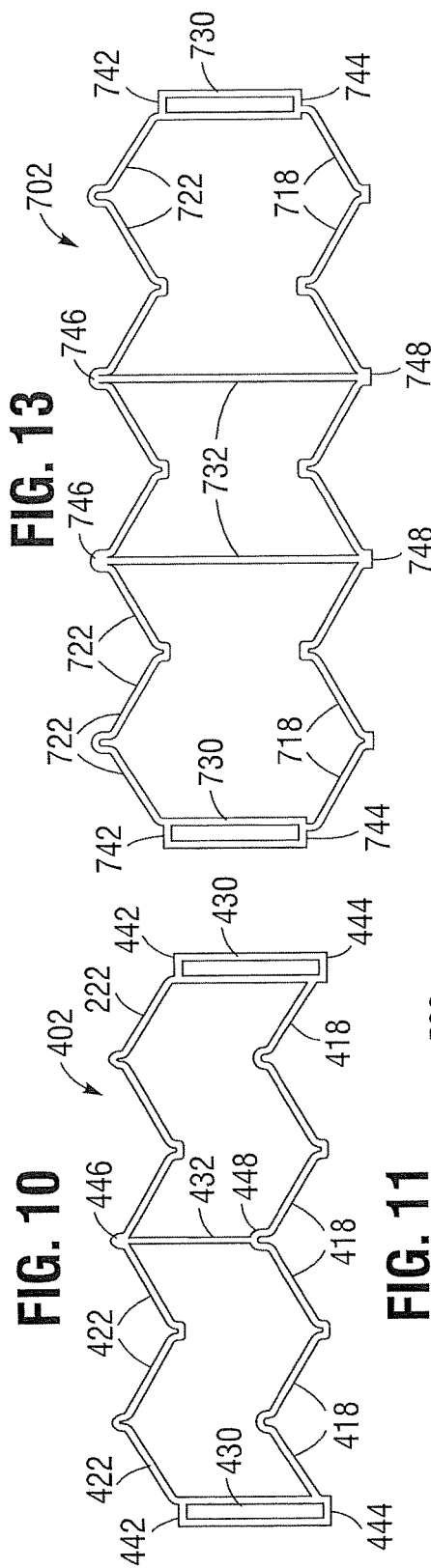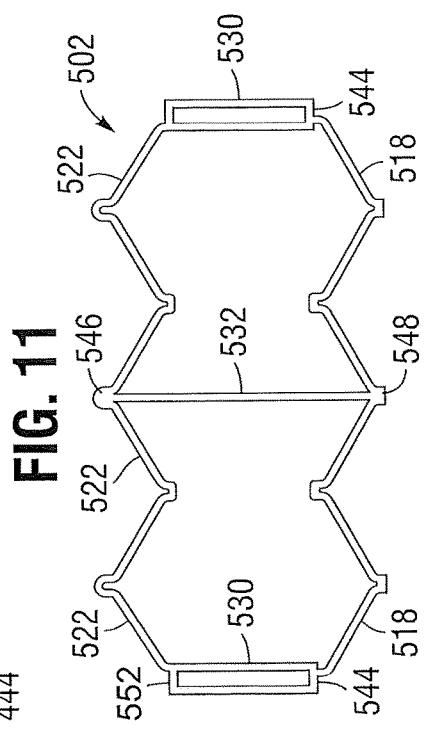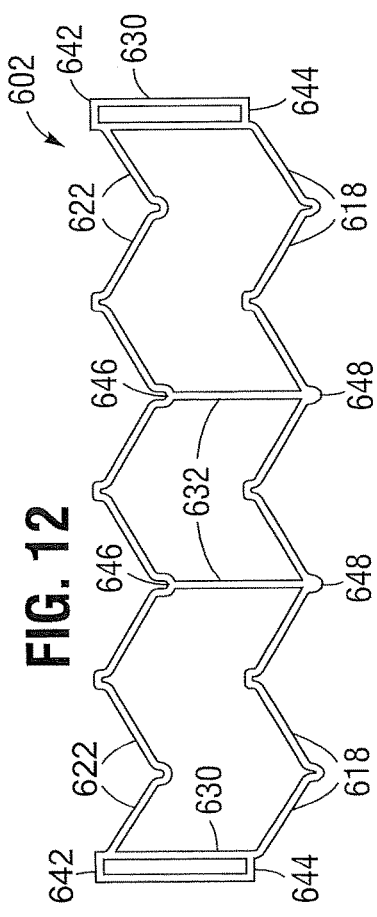

FLEXIBLE COMMISSURE FRAME

CROSS-REFERENCE TO RELATED APPLICATIONS

The present application is a Continuation of U.S. patent application Ser. No. 14/625,344, entitled, "FLEXIBLE COMMISSURE FRAME," filed Feb. 18, 2015, now U.S. Pat. No. 10,058,420, which claims the benefit of U.S. Provisional Application No. 61/941,123, filed Feb. 18, 2014. These applications are incorporated by reference herein.

FIELD

This disclosure is in the field of prosthetic heart valves, stents for use with prosthetic heart valves, and methods for delivering prosthetic heart valves.

BACKGROUND

Existing frames for prosthetic heart valves typically comprise rows of angled struts and a plurality of axial frame members spaced apart around the circumference of the frame. The plurality of axial frame members may comprise a plurality of leaflet attachment members (for attaching to the commissures of the supported valvular structure) and a multitude of axially directed struts extending between the rows of angled struts. A frame usually has three or more axially directed struts for every leaflet attachment member, and generally has no more than two angled struts located in between adjacent struts or other axial frame members. Indeed, having a large number of axially directed struts is perceived to be necessary for preserving the structural stability of the stent and/or valve. Unfortunately, having a large number of axial struts can come at the expense of valve flexibility.

A need therefore exists for stents and prosthetic valves that can have a high degree of flexibility, without compromising mechanical integrity or function.

SUMMARY

In one aspect of the disclosure, a prosthetic device for implantation at a cardiac valve annulus has an annular frame with an inflow end, an outflow end, and a plurality of axial frame members bridging two circumferentially extending rows of angled struts, wherein the plurality of axial frame members comprises a plurality of axially extending leaflet attachment members and a plurality of axial struts in a 1:1 ratio.

In some embodiments, the device can further comprise a leaflet structure positioned within the frame, the leaflet structure having a plurality of commissures that are secured to the frame at the leaflet attachment members.

In some embodiments, at least three angled struts separate adjacent axial frame members along each of the two rows of angled struts.

In some embodiments, exactly six angled struts separate adjacent leaflet attachment members along each of the two rows of angled struts, and exactly three angled struts separate adjacent axial frame members along each of the two rows of angled struts, such that each axial strut is positioned halfway between adjacent leaflet attachment members.

In some embodiments, each axial frame member extends between locations defined by the convergence of adjacent angled struts.

In some embodiments, the device further comprises an inner skirt secured to an interior portion of the annular frame, and an outer skirt secured to an exterior portion of the annular frame.

In some embodiments, the frame comprises exactly four rows of angled struts.

In some embodiments, the valve member comprises exactly three leaflets arranged in a tricuspid configuration, wherein the frame comprises exactly three axial struts and exactly three leaflet attachment members, and wherein the exactly three angled struts separate adjacent axial frame members along each of the two rows of angled struts.

In another aspect of the disclosure, an annular frame for a prosthetic heart valve can comprise an inflow end, an outflow end, and a plurality of axial frame members spaced angularly around the circumference of the frame. The plurality of axial frame members can bridge two circumferentially extending rows of angled struts, wherein each of the two rows comprise at least three angled struts between adjacent axial frame members.

In some embodiments, each of the two rows comprises exactly three angled struts between adjacent axial frame members.

In some embodiments, the plurality of axial frame members comprises a plurality of axially extending leaflet attachment members, and each of the two rows comprises exactly six angled struts between adjacent leaflet attachment members.

In some embodiments, the plurality of axial frame members comprises a plurality of axially extending leaflet attachment members, wherein each of the two rows comprises four angled struts between adjacent axial frame members and eight angled struts between adjacent leaflet attachment members.

In some embodiments, the plurality of axial frame members comprises exactly three leaflet attachment members and exactly three axial struts.

In some embodiments, the leaflet attachment members extend between locations defined by the convergence of the upper ends of adjacent angled struts of each row of angled struts, and the axial struts extend between locations defined by the convergence of the lower ends of adjacent angled struts of each row of angled struts.

In some embodiments, the two rows of angled struts can comprise a first row and a second row, wherein the first row is closer to the outflow end than the second row.

In some embodiments, the leaflet attachment members extend from locations defined by the convergence of the upper ends of adjacent angled struts along the first row of angled struts to locations defined by the convergence of the lower ends of adjacent angled struts along the second row of angled struts, and the axial struts extend between locations defined by the convergence of the lower ends of adjacent angled struts along the first row of angled struts to locations defined by the convergence of upper ends of adjacent angled struts along the second row of angled struts.

In some embodiments, the leaflet attachment members extend from locations defined by the convergence of the upper ends of adjacent angled struts along the first row of angled struts to locations defined by the convergence of the upper ends of adjacent angled struts along the second row of angled struts, and the axial struts extend between locations defined by the convergence of the lower ends of adjacent angled struts along the first row of angled struts to locations defined by the convergence of lower ends of adjacent angled struts along the second row of angled struts.

In some embodiments, the frame comprises exactly four rows of angled struts.

In another aspect of the disclosure, a prosthetic device for implantation at a cardiac valve annulus is provided, comprising an annular frame having an inflow end, an outflow end, at least four rows of circumferentially extending angled struts, and exactly six axial frame members bridging two rows of the four rows of circumferentially extending angled struts. The plurality of axial frame members can comprise exactly three axially extending leaflet attachment members and exactly three axial struts, wherein each of the two rows comprises exactly three angled struts between each adjacent pair of a leaflet attachment member and an axial strut, and exactly six angled struts between adjacent leaflet attachment members. The device can further comprise a tri-leaflet valve member positioned within the frame having commissures that are secured to the frame at the leaflet attachment members.

The foregoing and other objects, features, and advantages of the invention will become more apparent from the following detailed description, which proceeds with reference to the accompanying figures.

BRIEF DESCRIPTION OF THE DRAWINGS

FIGS. 1 and 2 show side and perspective views of an exemplary embodiment of a prosthetic heart valve.

FIGS. 3-5 show side, perspective, and flattened views of an exemplary frame of the prosthetic heart valve of FIG. 1.

FIGS. 7-8 show perspective and flattened views of an exemplary frame of the prosthetic heart valve of FIG. 6.

FIG. 9 shows a flattened view of another exemplary frame for a prosthetic heart valve.

FIG. 10 shows a flattened view of a portion of another exemplary frame for a prosthetic heart valve.

FIG. 11 shows a flattened view of a portion of another exemplary frame for a prosthetic heart valve.

FIG. 12 shows a flattened view of a portion of another exemplary frame for a prosthetic heart valve.

FIG. 13 shows a flattened view of a portion of another exemplary frame for a prosthetic heart valve.

DETAILED DESCRIPTION

Figure 5:
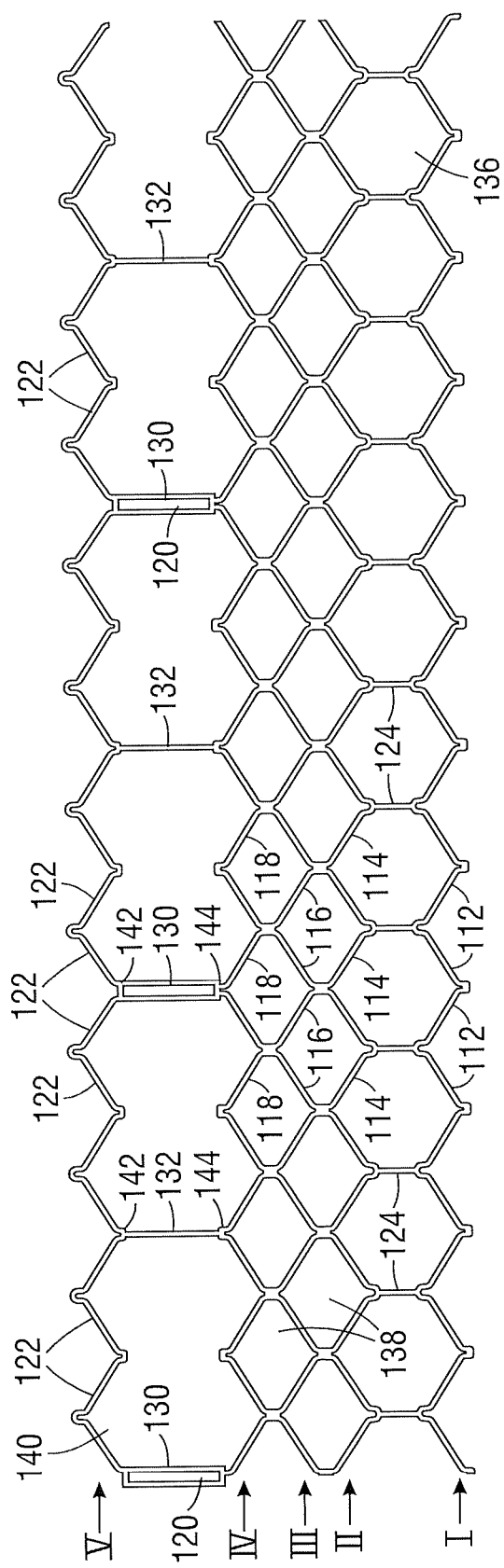

Disclosed herein are prosthetic heart valves and stents for use with such valves that are capable of a high degree of flexibility. This flexibility can be useful for delivery to the valve annulus (such as for crimping/expanding a transcatheter heart valve (THV)) and/or for accommodating movement of the valve during cardiac cycling. In particular embodiments, strategically selected locations around the circumference of the frame are without axial struts, resulting in the improved flexibility. In various embodiments, the flexibility of the commissures is enhanced as a result of an increase in the distance between each commissure and the nearest axial frame member (other than any support member located at the commissure such as a commissure support or window frame member). The frame can have one or more circumferentially extending rows of struts with three continuous angled struts between one or more pairs of axial supports. In some embodiments, these one or more rows of struts are located towards an outflow end of the frame. In some embodiments, the frame can have two rows of circumferentially extending struts (towards the outflow end of the valve) having three continuous angled struts between pairs of axial supports. In some embodiments, the frame has three continuous angled struts separating each commissure support (located at each commissure) from the nearest axial support. In another embodiment, there are four such angled struts separating each commissure support from the nearest axial strut.

As used herein, an "axial support" is a junction where at least three struts are connected, such as two angled struts connecting to a single axial strut or a junction of two angled struts and another axial member such as a commissure support. As used herein, an "axial frame member" is any axially extending support member that connects two (or more) circumferentially extending rows of angled struts. Thus, an axial frame member can be an axial support member that engages one or more leaflets, such as a commissure support. An axial frame member can also be a simple axial strut or other axial member that does not engage a leaflet. As used herein, a "commissure support" (also referred to as a "leaflet attachment member") is an axially extending support member configured to support a respective commissure of a prosthetic valve member. A commissure support can be a commissure "window frame member" configured to receive a commissure of a prosthetic valve member through an opening in the frame member, as further described below. A commissure support can also be an axial strut or other axial support member that does not include a window or other opening sized to receive a commissure. As such, a commissure can be supported by a leaflet attachment member using various techniques or mechanisms, such as by securing commissures to respective leaflet attachment members with sutures extending through suture openings in the leaflet attachment members.

FIGS. 1-2 show a prosthetic heart valve 100, according to one embodiment in side view and in perspective, respectively. The illustrated prosthetic valve is adapted to be implanted in the native aortic annulus, although in other embodiments it can be adapted to be implanted in the other native annuluses of the heart (i.e., the native mitral, pulmonary, and tricuspid valves) or in other tubular passageways in the body. The valve 100 can have four main components: a stent or frame 102, a valvular structure 104, an inner skirt 106, and an outer skirt 108. The frame 102 can have an inflow end 103 and an outflow end 105.

The valvular structure 104 can comprise three leaflets 110, collectively forming a leaflet structure, which can be arranged to collapse in a tricuspid arrangement. The leaflets 110 can be secured to one another at their adjacent sides to form commissures. The leaflets 110 can be formed of pericardial tissue (e.g., bovine pericardial tissue), biocompatible synthetic materials, or various other suitable natural or synthetic materials as known in the art and described in U.S. Pat. No. 6,730,118, which is incorporated by reference herein.

The bare frame 102 is shown in FIGS. 3-5 in a side view, a perspective view, and an unrolled and flattened configuration, respectively. The frame 102 can be formed with a plurality of circumferentially spaced slots, or commissure windows 120 (three in the illustrated embodiment), that are adapted to mount the commissures of the valvular structure 104 to the frame, as described in greater detail below. The frame 102 can be made of any of various suitable plastically-expandable materials (e.g., stainless steel, etc.) or self-expanding materials (e.g., nitinol) as known in the art.

Suitable plastically-expandable materials that can be used to form the frame 102 can include, without limitation, stainless steel, a nickel based alloy (e.g., a cobalt-chromium or a nickel-cobalt-chromium alloy), polymers, or combinations thereof. In particular embodiments, the frame 102 can be made of a nickel-cobalt-chromium-molybdenum alloy, such as MP35N® alloy (SPS Technologies), which is equivalent to UNS R30035 alloy (covered by ASTM F562-02). MP35N®/UNS R30035 alloy comprises 35% nickel, 35% cobalt, 20% chromium, and 10% molybdenum, by weight. It has been found that the use of MP35N® alloy to form the frame 102 can provide superior structural results over stainless steel. In particular, when MP35N® alloy is used as the frame material, less material is needed to achieve the same or better performance in radial and crush force resistance, fatigue resistances, and corrosion resistance. Moreover, since less material is required, the crimped profile of the frame 102 can be reduced, thereby providing a lower profile valve assembly for percutaneous delivery to the treatment location in the body.

When constructed of a plastically-expandable material, the frame 102 (and thus the valve 10) can be crimped to a radially compressed state on a delivery catheter and then expanded inside a patient by an inflatable balloon or equivalent expansion mechanism. When constructed of a self-expandable material, the frame 102 (and thus the valve 100) can be crimped to a radially compressed state and restrained in the compressed state by insertion into a sheath or equivalent mechanism of a delivery catheter. Once inside the body, the valve can be advanced from the delivery sheath, which allows the valve to expand to its functional size.

Referring to FIG. 5, the frame 102 (shown in a flattened configuration) in the illustrated embodiment comprises a first, lower row I of angled struts 112 arranged end-to-end and extending circumferentially at the inflow end of the frame; a second row II of circumferentially extending, angled struts 114; a third row III of circumferentially extending, angled struts 116; a fourth row IV of circumferentially extending, angled struts 118; and a fifth row V of circumferentially extending, angled struts 122 at the outflow end 105. A plurality of substantially straight, axially extending struts 124 can be used to interconnect the struts 112 of the first row I with the struts 114 of the second row II. The fifth row V of angled struts 122 are connected to the fourth row IV of angled struts 118 by a plurality of axially extending window frame portions 130 (which define the commissure windows 120) and a plurality of axially extending struts 132.

Each commissure window frame portion 130 mounts a respective commissure of the valvular structure 104. As can be seen, each window frame portion 130 is secured at its upper and lower ends to the adjacent rows of angled struts to provide a robust configuration that enhances fatigue resistance under cyclic loading of the valve compared with known frames using cantilevered struts for supporting the commissures of the leaflet structure. This configuration enables a reduction in the frame wall thickness to achieve a smaller crimped diameter of the valve. In particular embodiments, the thickness of the frame 12 as measured between the inner diameter and outer diameter is about 0.48 mm or less.

As best shown in FIGS. 3-4, the struts and frame portions of the frame collectively define a plurality of open cells of the frame. At the inflow end of the frame 102, struts 112, struts 114, and struts 124 define a lower row of cells defining openings 136. The second, third, and fourth rows of struts 114, 116, and 118 define two intermediate rows of cells defining openings 138. The fourth and fifth rows of struts 118 and 122, along with window frame portions 130 and struts 132, define an upper row of cells defining openings 140. The openings 140 are relatively large and are sized to allow portions of the valvular structure 104 to protrude, or bulge, into and/or through the openings 140 when the frame 102 is crimped in order to minimize the crimping profile.

In some embodiments, there are fewer than three axially extending struts 132 between adjacent window frame portions 130, along the length of the rows, such as only two axially extending struts 132 or only one axially extending strut 132. In some embodiments, there is only one axially extending strut 132 in between adjacent window frame portions 130, which can be located halfway in between the window frame portions 130. Thus, in various embodiments, the frame can be specifically constructed to integrate window frame portions 130 and axially extending struts 132 in a 1:1 ratio.

In one embodiment illustrated in FIGS. 3-5, there are exactly three window frame portions 130 and exactly three axial struts 132. Minimizing or reducing the number of axially extending struts 132 between window frame portions 130 promotes more compact crimping of the prosthetic valve. This also maximizes or increases the size of openings 140, which, for example, is advantageous in cases where the outflow end 105 of the prosthetic valve extends higher than the level of the coronary ostia. In such cases, the larger openings 140 can provide access to the coronary arteries for future procedures, such as procedures requiring catheterization of the coronary arteries.

Each window frame portion 130 and/or each axially extending strut 132 can each extend between locations 142 characterized by the convergence of the lower ends of two angled struts 122 (of row V, at the outflow end 105) to locations or nodes 144 defined by the convergence of the upper ends of two angled struts 118 (of row IV). There can be two angled struts 122 along row V from one location 142 to the next location 142, and two angled struts 118 along row IV from one location 144 to the next location 144.

The frame 102 can comprise an axially extending frame member (i.e., a frame portion 130 or a strut 132) at every other such pair of such locations 142, 144 along the rows V and VI, respectively. The frame 102 can have a window frame portion 130 every four such locations, and spaced equally apart around the circumference of the frame 102, which can provide for a total of three window frame portions 130 (corresponding to the three commissures in a tri-leaflet valve). Thus, the frame 102 can comprise, in sequence along the row V, a window frame portion 130 extending between a pair of such locations 142, 144 followed next by a second pair of locations 142, 144 lacking an axially extending strut or frame member extending therebetween, followed then by an axially extending strut 132 extending between a third pair of locations 142, 144, followed then by a fourth pair of locations 142, 144 again lacking an axially extending strut or frame member, followed by another window frame portion 130 extending between a pair of such locations 142, 144 (and thus re-starting the sequence of struts and frame portions). With two angled struts (along each of rows IV and V) between each set of locations 142, 144, this embodiment can thus have sets of eight angled struts between adjacent window frame portions 130, along each row, with four continuous angled struts between each window frame portion 130 and its adjacent axial struts 132 (i.e., no other axial frame members in between).

After the prosthetic heart valve 100 is properly implanted at the valve annulus, the prosthetic valve 100 can cycle between open and closed states to permit or restrict the flow of blood. In various embodiments, the frame 102 of the prosthetic heart valve 100 provides a measure of damping during valve closure by bending inwards during diastole, which relieves stress on the leaflets. For example, forces that pull the commissures of the leaflets 110 radially inwards (such as during valve closure) can also pull areas of the frame immediately adjacent the commissures (such as the window frame portions 130) radially inward, while the axial struts 132 can be urged radially outward. In various embodiments, this damping effect (including pulling of the frame portions 130 radially inward and pushing of the axial struts 132 radially outward) is enhanced by reducing the number of axial struts present along the top rungs (between rows IV and V in valve 100) as disclosed herein, relative to frames having a greater number of axial frame members (e.g., greater number of axial struts).

The main functions of the inner skirt 106 are to assist in securing the valvular structure 104 to the frame 102 and to assist in forming a good seal between the valve 100 and the native annulus by blocking the flow of blood through the open cells of the frame 102 below the lower edge of the leaflets 110. The inner skirt 106 desirably comprises a tough, tear resistant material such as polyethylene terephthalate (PET), although various other synthetic or natural materials can be used. The inner skirt 106 can be secured to the inside of the frame 102 via sutures. The valvular structure 104 can be attached to the inner skirt 106 with the assistance of one or more thin PET reinforcing strips (which collectively can form a sleeve, not pictured), which can enable secure suturing and protect the pericardial tissue of the leaflet structure from tearing. The valvular structure 104 can be sandwiched between the inner skirt 106 and the thin PET strips.

The upper edge portion of the inner skirt 106 can be formed with a plurality of projections that define an undulating shape that generally follows the shape of the fourth row of struts 118 (row IV) immediately adjacent the lower ends of axial struts 132. In this manner, as best shown in FIG. 1, the upper edge of inner skirt 106 can be tightly secured to struts 118 with suture 146. The inner skirt 106 can also be secured to the first, second, and/or third rows of struts 112, 114, and 116 (rows I-III), respectively, with suture 146.

The inner skirt 106 can be sutured to the frame 102 at locations away from the suture line attaching the lower edges of the leaflets 110 to the inner skirt 106, which both reduces concentration of stress at the leaflet-suture-line and increases pliability to the skirt in that area.

As shown in FIGS. 1-2, a plurality of flexible connectors 125 can be used to interconnect each pair of adjacent edges of the leaflets 110 and to mount the leaflets 110 to the commissure window frame portions 130. The flexible connectors 125 can be made from a piece of woven PET fabric, although other synthetic and/or natural materials can be used. Each commissure can comprise two tab portions of two adjacent leaflets. Each commissure can be secured to the frame, for example, by inserting the tab portions through the commissure windows 120 of the window frame portions 130, and suturing the tab portions to a connector 125 outside of the frame 102.

The outer skirt 108 can be laser cut or otherwise formed from a strong, durable piece of material, such as woven PET, although other synthetic or natural materials can be used. The outer skirt 108 can have a substantially straight lower edge and an upper edge defining a plurality of alternating projections 150 and notches 152. The lower edge of the outer skirt 108 can be sutured to the lower edge of the inner skirt 106 at the inflow end of the valve 100. In other embodiments, the inner skirt 106 and outer skirt 108 are integrally manufactured as a single component. As shown in FIGS. 1-2, each projection 150 can be affixed to the second rung II of struts 114 of the frame 102 with sutures 154.

Additional details relevant to the securing of the valve member 104, inner skirt 106 and outer skirt 108 to the frame 102 are provided in U.S. Patent Publication 2011/0123529, which is incorporated by reference in its entirety.

In various embodiments, a frame can be constructed to have greater or fewer rows of angled struts than in frame 102, such as four or six rows of angled struts. In various other frame embodiments, each window frame portion and/or each axially extending strut can extend between two locations each defined by the convergence of the upper ends of angled struts. In various embodiments, each window frame portion and/or each axially extending strut can extend between two locations each defined by the convergence of the lower ends of angled struts.

Figure 6:
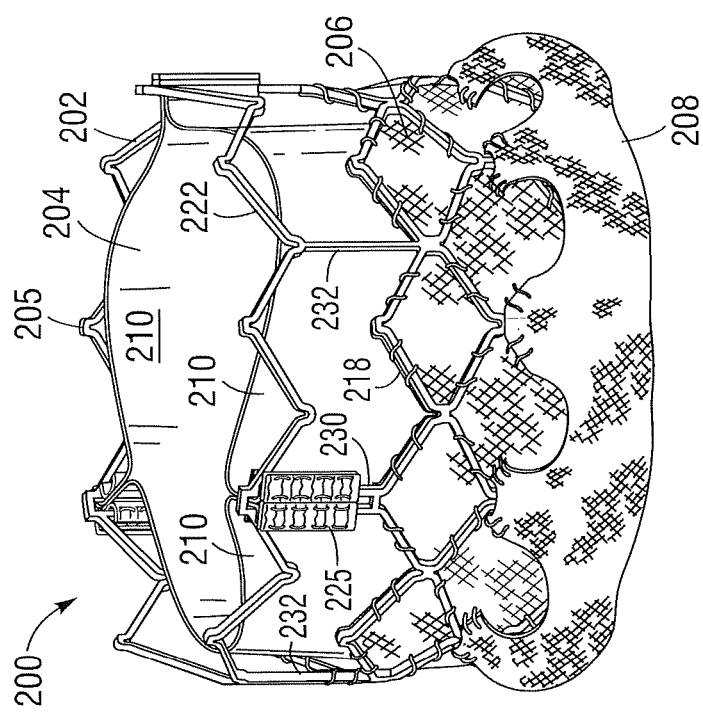
FIG. 6 is a perspective view of another exemplary prosthetic heart valve.

FIG. 6 shows a perspective view of another exemplary prosthetic valve 200 with an inner skirt 206, an outer skirt 208, and a valve member 204 mounted within a stent 202. The valve member 204 can have a set of three leaflets 210. A plurality of flexible connectors 225 can be used to interconnect pairs of adjacent edges of the leaflets 210 and to mount the leaflets 210 to the commissure window frame portions 230.

Figure 7:
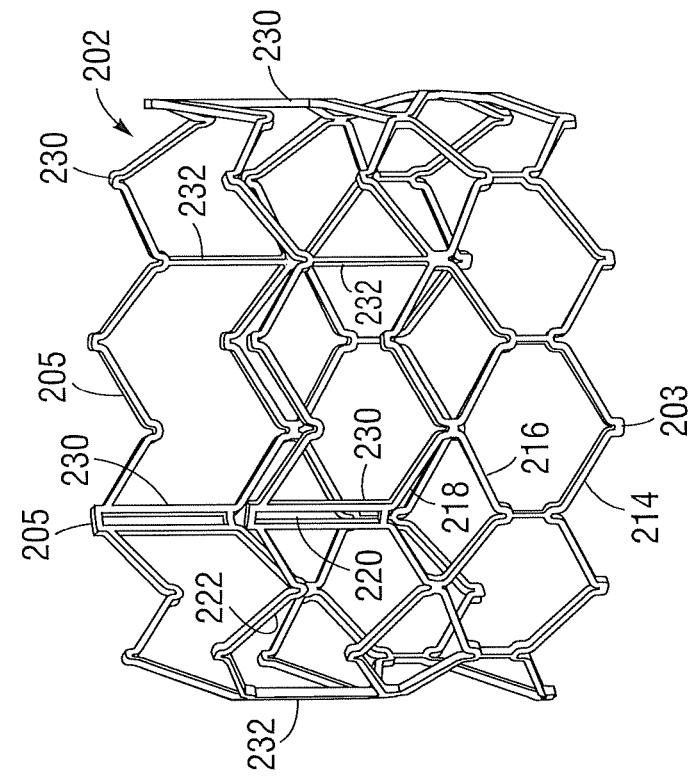

FIGS. 7-8 show perspective and flattened, unrolled views of the bare stent 202 having an inflow end 203, an outflow end 205, and four rows (I-IV) of struts 214, 216, 218, 222 (instead of five rows as shown in FIGS. 1-5). The fourth row IV of angled struts 222 can be connected to the third row IV of angled struts 218 by a plurality of axially extending window frame portions 230 (which define commissure windows 220) and a plurality of axially extending struts 232.

Thus, each window frame portion 230 and each axially extending strut 232 can extend between the two rows of angled struts that are closest to the outflow end 205. In particular, each window frame portion 230 can extend between a location 242 defined by the convergence of the upper ends of two angled struts 222 and a location 244 defined by the convergence of the upper ends of two angled struts 218. Each axially extending strut 232 can extend between another location 246 defined by the convergence of the lower ends of two angled struts 222 and another location 248 defined by the convergence of the lower ends of two angled struts 218.

The frame 202 can comprise three window frame portions 230 spaced equally apart around the circumference of the frame 202. As shown, the frame 202 can be constructed to have six angled struts (along each of rows III and IV) between the window frame portions 230 along each row. The frame can be constructed to have three angled struts between each window frame portion 230 and the adjacent axial struts 232. Thus, each axial strut 232 can be located halfway between adjacent window frame portions 230, and the frame 200 can be constructed to integrate window frame portions and axially extending struts in a 1:1 ratio. In the illustrated embodiment, there are exactly three window frame portions 230 and exactly three axial struts 232.

In particular, the frame 202 can comprise, in sequence along the rows III and IV, a window frame portion 230 extending between a pair of locations 242, 244, followed by a pair of locations 246, 248 lacking an axially extending member, followed by a pair of locations 242, 244 lacking an axially extending member, followed by an axially extending strut 232 extending between a pair of locations 246, 248, followed by a pair of locations 242, 244 lacking an axially extending member, followed by a pair of locations 246, 248 lacking an axially extending member, followed by another window frame portion 230 extending between a pair of locations 242, 244 (and thus re-starting the sequence of window frame portions 230 and axially extending struts 232).

Once the prosthetic heart valve 200 is properly installed at the valve annulus, the valve 200 can cycle between open and closed states to permit or restrict the flow of blood. As discussed with respect to prosthetic valve 100, forces that pull the commissures radially inwards during cycling can also pull the window frame portions 230 radially inward to relieve stress on the leaflets during valve closure. Meanwhile, the axial struts 232 can be urged radially outward.

The frame 200 can be capable of assuming a collapsed configuration (such as for delivery on or within a catheter) and an expanded configuration (i.e., functional configuration at the valve annulus). In various embodiments, in the collapsed configuration, the plurality of axial struts is positioned radially outwards relative to the leaflet attachment members and/or commissures. In one embodiment, in the process of transitioning from an expanded configuration to a collapsed configuration and/or from an collapsed configuration to an expanded configuration, the valve 200 can assume an intermediate configuration in which only those struts 222 of row IV that are adjacent to an axially extending strut 232 are brought together to extend axially (side-by-side and in substantial axial alignment with struts 232).

In another embodiment, as shown in FIG. 9, a frame 302 can have axial window frame members 330 extending between locations 342 defined by the convergence of the upper ends of two angled struts 322 and locations 344 defined by the convergence of the lower ends of two angled struts 318. The frame 302 can have axially extending struts 332 extending between locations 346 defined by the convergence of the lower ends of two angled struts 322 and locations 348 defined by the convergence of the upper ends of two angled struts 318.

Frame 302 is similar to frame 202 except that the first three rows of angled struts (rows I, II, and III) are shifted 20 degrees relative to the same rows of frame 202. Thus, each window frame member 330 is axially aligned with a location 344 defined by the convergence of the lower ends of two angled struts 318 of row III. Each window frame member 330 can comprise a lower strut portion 334 below the level of the commissure window 320 (towards the inflow end of the stent 302). This lower strut portion 334 extends from the lower end of a window frame member 330 to a location 344 defined by the convergence of the lower ends of two angled struts 318. The lower strut portion 334 provides added length to the window frame member 330 and allows the frame member 330 to effectively bridge the larger distance between locations 342, 344 in this embodiment. Other features and components of frame 302 can be similar to as described above for frame 202.

FIG. 10 shows a portion of a frame 402, according to another embodiment. In FIG. 10, only one-third of the circumference of the two upper rows of angled struts (the rows closest to the outflow end) is shown. The frame 402 can have axial window frame members 430 extending between locations 442 defined by the convergence of the lower ends of two angled struts 422 and locations 444 defined by the convergence of the lower ends of two angled struts 418. The frame 402 can have axially extending struts 432 extending between locations 446 defined by the convergence of the upper ends of two angled struts 422 and locations 448 defined by the convergence of the upper ends of two angled struts 418.

The two upper rows of angled struts includes a total of three axial window frame members 430 and a total of three axially extending struts 432 located equidistant between the window frame members 430 with three angled struts 418 and three angled struts 422 extending between a window frame member 430 and an adjacent axially extending strut 432. The frame 402 can also include three additional rows of angled struts located at the inflow end of the frame (not shown in FIG. 10), similar to embodiments discussed above. The lower end of each window frame member 430 can be connected to the upper ends of two angled struts of an adjacent row (the third row from the outflow end of the frame) at a location 444. Thus, in this embodiment, the lower end of each axially extending strut 432 is not connected to any struts of the adjacent row.

FIG. 11 shows a portion of a frame 502, according to another embodiment. In FIG. 11, only one-third of the circumference two upper rows of angled struts (the rows closest to the outflow end) are shown. The frame 502 can have axial window frame members 530 extending between locations 542 defined by the convergence of the lower ends of two angled struts 552 and locations 554 defined by the convergence of the upper ends of two angled struts 518. The frame 502 can have axially extending struts 532 extending between locations 546 defined by the convergence of the upper ends of two angled struts 522 and locations 548 defined by the convergence of the lower ends of two angled struts 518. The axially extending struts 532 in this embodiment can be longer than the window frame members 530 to account for the greater distance between locations 546, 548 compared to the distance between locations 542, 544.

The two upper rows of angled struts includes a total of three axial window frame members 530 and a total of three axially extending struts 532 located equidistant between the window frame members 530 with three angled struts 518 and three angled struts 522 extending between a window frame member 530 and an adjacent axially extending strut 532. The frame 502 can also include three additional rows of angled struts located at the inflow end of the frame (not shown in FIG. 11), similar to embodiments discussed above. The lower end of each axially extending strut 532 can be connected to the upper ends of two angled struts of an adjacent row (the third row from the outflow end of the frame) at a location 548. Thus, in this embodiment, the lower end of each window frame member 530 is not connected to any angled struts of the adjacent row.

FIG. 12 shows a portion of a frame 602, according to another embodiment. In FIG. 12, only one-third of the circumference of the two upper rows of angled struts (the rows closest to the outflow end) is shown. The frame 602 can have axial window frame members 630 extending between locations 642 defined by the convergence of the upper ends of two angled struts 622 and locations 644 defined by the convergence of the upper ends of two angled struts 618. The frame 602 can have axially extending struts 632 extending between locations 646 defined by the convergence of the lower ends of two angled struts 622 and locations 648 defined by the convergence of the lower ends of two angled struts 618.

In the embodiment of FIG. 12, there are two such axially extending struts 632 spaced between each pair of window frame members 630. In particular, for each pair of window frame members, there are three angles struts 618 and three angles struts 622 between each window frame member 630 and the closest axially extending strut 632, and two angles struts 618 and two angles struts 622 between the two axially extending struts 632. Thus, for the entire frame 602, the two upper rows of angled struts includes a total of three axial window frame members 630 and a total of six axially extending struts 632.

The frame 602 can also include three additional rows of angled struts located at the inflow end of the frame (not shown in FIG. 12), similar to embodiments discussed above. The lower end of each axially extending strut 632 can be connected to the upper ends of two angled struts of an adjacent row (the third row from the outflow end of the frame) at a location 648. Thus, in this embodiment, the lower end of each window frame member 630 is not connected to any struts of the adjacent row.

FIG. 13 shows a portion of a frame 702, according to another embodiment. In FIG. 13, only one-third of the circumference of the two upper rows of angled struts (the rows closest to the outflow end) is shown. The frame 702 can have axial window frame members 730 extending between locations 742 defined by the convergence of the lower ends of two angled struts 722 and locations 744 defined by the convergence of the upper ends of two angled struts 718. The frame 702 can have axially extending struts 732 extending between locations 746 defined by the convergence of the upper ends of two angled struts 722 and locations 748 defined by the convergence of the lower ends of two angled struts 718.

In the embodiment of FIG. 13, there are two such axially extending struts 732 spaced between each pair of window frame members 730. In particular, for each pair of window frame members, there are three angles struts 718 and three angles struts 722 between each window frame member 730 and the closest axially extending strut 732, and two angles struts 718 and two angles struts 722 between the two axially extending struts 732. Thus, for the entire frame 702, the two upper rows of angled struts includes a total of three axial window frame members 730 and a total of six axially extending struts 732. Also, struts 732 can be longer than window frame members 730 to account for the greater distance between locations 746, 748 compared to the distance between locations 742, 744.

The frame 702 can also include three additional rows of angled struts located at the inflow end of the frame (not shown in FIG. 13), similar to embodiments discussed above. The lower end of each axially extending strut 732 can be connected to the upper ends of two angled struts of an adjacent row (the third row from the outflow end of the frame) at a location 748. Thus, in this embodiment, the lower end of each window frame member 730 is not connected to any struts of the adjacent row.

The prosthetic valve embodiments disclosed herein can be surgically implanted and/or can be delivered using a delivery apparatus, such as a catheter. The prosthetic valve can be mounted in a crimped state on or adjacent an inflatable balloon or equivalent expansion mechanism of the delivery apparatus. The delivery apparatus and crimped prosthetic valve can be inserted into the patient's vasculature and advanced through the patient's body using known techniques.

In one implementation, the prosthetic valve is delivered in a transfemoral procedure in which the delivery apparatus is inserted into a femoral artery and advanced through the aorta to the native aortic valve (or another native valve of the heart). In another implementation, the prosthetic valve can be delivered in a transventricular procedure in which the delivery apparatus is inserted through a small surgical opening in the chest and another surgical opening in the wall of the heart, such as the wall of the left ventricle. In another implementation, the prosthetic valve can be delivered in a transaortic procedure in which the delivery apparatus is inserted through a small surgical opening in the chest and another surgical opening in the ascending aorta, at a location above the aortic valve. In another implementation, the prosthetic valve is a replacement venous valve for implantation in a vein, or a replacement for another valve with a lower flow rate relative to the aortic valve.

When the prosthetic valve is positioned at the desired deployment location (e.g., within the native aortic valve), the balloon of the delivery apparatus can be inflated to radially expand the prosthetic valve. In some embodiments, upon full expansion of the prosthetic valve, the outer skirt of the prosthetic valve can be forced into contact with the surrounding tissue of the native valve, establishing a seal between the outer surface of the frame and the surrounding tissue. The frame of the prosthetic valve, when in the radially compressed, mounted configuration, can comprise an inflow end portion that has an outer diameter that is smaller than the outer diameter of the outflow end portion of the frame.

When constructed of a self-expanding material, the prosthetic valve can be crimped to a radially compressed state and restrained in the compressed state by insertion into a sheath or equivalent mechanism of a delivery catheter. After the delivery apparatus is inserted into the body and advanced to position the prosthetic valve at the desired deployment location, the prosthetic valve can be advanced from the delivery sheath. As the prosthetic valve is deployed from the delivery sheath, the prosthetic valve can radially self-expand to its functional size.

The prosthetic heart valve can comprise commissure portions of the leaflets extending radially outwardly through corresponding window frame portions to locations outside of the frame and sutured to the side struts of the commissure window frame. To minimize the crimp profile of the prosthetic valve, the window frame portions can be depressed radially inwardly relative to the surrounding portions of the frame, such as the frame portions extending between adjacent commissure windows, when the prosthetic valve is radially compressed to the collapsed configuration on a catheter.

For example, the commissure windows of the frame can be depressed inwardly a radial distance, such as between 0.2 mm and 1.0 mm, relative to the portions of the frame extending between adjacent commissure windows when the prosthetic valve is radially collapsed. In this way, the outer diameter of the outflow end portion the prosthetic valve comprising the commissure portions can be generally consistent, as opposed to the commissure portions jutting outward from the surrounding portions of the prosthetic valve, which could hinder delivery of the prosthetic valve into the body. Even with the radially depressed commissure window frames, the outer diameter of the inflow end portion of the frame can still be smaller than, or about equal to, the outer diameter of the outflow end portion of the frame when the prosthetic valve is radially collapsed on the catheter, allowing for a minimal or reduced maximum overall diameter of the prosthetic valve. By minimizing or reducing the diameter of the prosthetic valve when mounted on the delivery catheter, the diameter of a delivery catheter through which the prosthetic valve is advanced can also be minimized or reduced. This allows the prosthetic valve to be delivered through smaller vessels in the body, making the delivery procedure less invasive, in general.

Additional details relevant to delivery of the prosthetic heart valves disclosed herein are provided in U.S. Patent Publication 2011/0123529, which is incorporated herein by reference.

General Considerations

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached drawings may not show the various ways in which the disclosed methods can be used in conjunction with other methods. As used herein, the terms "a", "an", and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A", "B", "C", "A and B", "A and C", "B and C", or "A, B, and C".

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. I therefore claim as my invention all that comes within the scope and spirit of these claims.

I claim:

1. An annular frame for a prosthetic heart valve, the annular frame comprising:
    an inflow end;
    an outflow end;
    a first row of angled struts defining the outflow end;
    a second row of angled struts being closer to the inflow end than the first row of angled struts;
    a third row of angled struts being closer to the inflow end than the second row of angled struts; and
    a plurality of axial frame members bridging the first and second rows of angled struts;
    wherein the plurality of axial frame members have respective first ends and second ends, the first ends being linked by the first row of angled struts and the second ends being linked by the second row of angled struts;
    wherein the plurality of axial frame members comprises a plurality of axially extending commissure supports configured to support respective commissures of leaflets of the prosthetic heart valve and one or more axial struts located between any two commissure supports;
    wherein at least three angled struts in the first row separate at least one commissure support and an immediately adjacent axial strut in a circumferential direction;
    wherein each axial strut bridges the first and second rows of angled struts, and is straight and extends parallel to the commissure supports along the entire length of the axial strut.

2. The annular frame of claim 1, further comprising a fourth row of angled struts defining the inflow end.

3. The annular frame of claim 1, wherein there is exactly one axial strut located between any pair of commissure supports comprising a first commissure support and a second commissure support nearest to the first commissure support in the circumferential direction.

4. The annular frame of claim 1, wherein there are at least three angled struts in the first row between any two immediately adjacent axial frame members in the circumferential direction.

5. The annular frame of claim 4, wherein there are exactly three angled struts in the first row between any two immediately adjacent axial frame members in the circumferential direction.

6. The annular frame of claim 4, wherein there are exactly four angled struts in the first row between any two immediately adjacent axial frame members in the circumferential direction.

7. The annular frame of claim 1, wherein there is exactly one pair of axial struts located between any pair of commissure supports comprising a first commissure support and a second commissure support nearest to the first commissure support in a circumferential direction.

8. The annular frame of claim 7, wherein there are exactly two angled struts in the first row between the exactly one pair of axial struts.

9. The annular frame of claim 7, wherein there are exactly three angled struts in the first row between each commissure supports and any of its immediately adjacent axial struts in the circumferential direction.

10. The annular frame of claim 1, wherein a convergence of immediately adjacent angled struts in the first row defines a first set of alternating upper ends and lower ends, and a convergence of immediately adjacent angled struts in the second row defines a second set of alternating upper ends and lower ends.

11. The annular frame of claim 10, wherein the upper ends and lower ends in the first set are axially aligned with the upper ends and lower ends in the second set, respectively.

12. The annular frame of claim 10, wherein the upper ends and lower ends in the first set are axially aligned with the lower ends and upper ends in the second set, respectively.

13. The annular frame of claim 10, wherein each commissure support extends between an upper end in the first set and a corresponding upper end in the second set.

14. The annular frame of claim 10, wherein each commissure support extends between a lower end in the first set and a corresponding lower end in the second set.

15. The annular frame of claim 10, wherein each commissure support extends between a lower end in the first set and a corresponding upper end in the second set.

16. The annular frame of claim 10, wherein each commissure support extends between an upper end in the first set and a corresponding lower end in the second set.

17. The annular frame of claim 10, wherein the axial struts are longer than the commissure supports.

18. The annular frame of claim 10, wherein the axial struts are shorter than the commissure supports.

19. The annular frame of claim 10, wherein the axial struts have about the same length as the commissure supports.

20. An annular frame for a prosthetic heart valve, the annular frame comprising:
- an inflow end;
- an outflow end;
- a first row of angled struts defining the outflow end;
- a second row of angled struts being closer to the inflow end than the first row of angled struts;
- a third row of angled struts being closer to the inflow end than the second row of angled struts; and
- a plurality of axial frame members bridging the first and second rows of angled struts;

wherein the plurality of axial frame members have respective first ends and second ends, the first ends being linked by the first row of angled struts and the second ends being linked by the second row of angled struts;

wherein the plurality of axial frame members comprises a plurality of axially extending commissure supports configured to support respective commissures of leaflets of the prosthetic heart valve and one or more axial struts located between any two commissure supports in a circumferential direction;

wherein a ratio of the number of angled struts in the first row to the number of axial frame members is greater than 2:1;

wherein each axial strut bridges the first and second rows of angled struts, and is straight and extends parallel to the commissure supports along the entire length of the atrial strut.

21. The annular frame of claim 20, wherein the number of axial struts and the number of commissure supports have a 1:1 ratio.

22. The annular frame of claim 20, wherein the number of axial struts and the number of commissure supports have a 2:1 ratio.

23. The annular frame of claim 20, wherein there are at least three angled struts in the first row between any two immediately adjacent axial frame members in the circumferential direction.

24. The annular frame of claim 20, wherein at least three angled struts in the first row separate at least one commissure support and an immediately adjacent axial strut in the circumferential direction.

\* \* \* \* \*